US009011410B2

(12) United States Patent
Marsala

(10) Patent No.: US 9,011,410 B2
(45) Date of Patent: Apr. 21, 2015

(54) SPINAL MULTISEGMENTAL CELL AND DRUG DELIVERY SYSTEM

(75) Inventor: Martin Marsala, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 922 days.

(21) Appl. No.: 12/598,667

(22) PCT Filed: May 2, 2008

(86) PCT No.: PCT/US2008/062529
§ 371 (c)(1),
(2), (4) Date: Apr. 9, 2010

(87) PCT Pub. No.: WO2008/137760
PCT Pub. Date: Nov. 13, 2008

(65) Prior Publication Data
US 2010/0198189 A1    Aug. 5, 2010

Related U.S. Application Data

(60) Provisional application No. 60/915,743, filed on May 3, 2007.

(51) Int. Cl.
| | |
|---|---|
| A61M 31/00 | (2006.01) |
| A61M 5/178 | (2006.01) |
| A61M 5/00 | (2006.01) |
| A61M 25/00 | (2006.01) |
| A61B 17/34 | (2006.01) |

(52) U.S. Cl.
CPC ................................ *A61B 17/3472* (2013.01)

(58) Field of Classification Search
CPC ....... A61M 5/158; A61M 5/46; A61M 5/178; A61M 25/01; A61M 25/06; A61M 25/065; A61M 5/32; A61M 5/3286; A61B 17/3403; A61B 17/3478
USPC ........... 604/506, 507, 510, 511, 264, 187, 19, 604/21, 131, 164.01, 181; 600/34; 435/366
See application file for complete search history.

(56) References Cited

U.S. PATENT DOCUMENTS

| | | | | |
|---|---|---|---|---|
| 5,364,374 | A * | 11/1994 | Morrison et al. | 604/272 |
| 5,810,788 | A * | 9/1998 | Racz | 604/272 |
| 6,273,877 | B1 * | 8/2001 | West et al. | 604/264 |
| 2003/0032929 | A1 * | 2/2003 | McGuckin, Jr. | 604/272 |
| 2003/0199085 | A1 * | 10/2003 | Berger et al. | 435/366 |
| 2005/0085790 | A1 * | 4/2005 | Guest et al. | 604/506 |
| 2006/0205999 | A1 * | 9/2006 | Berger et al. | 600/34 |

\* cited by examiner

*Primary Examiner* — Bhisma Mehta
*Assistant Examiner* — Bradley G Thomas, Jr.
(74) *Attorney, Agent, or Firm* — TechLaw LLP

(57) ABSTRACT

Delivery devices and methods related thereto may be used in humans for spinal delivery of cells, drugs or vectors. The patient population may include patients with spinal traumatic injury, amyotrophic lateral sclerosis, multiple sclerosis, spinal ischemia and any other spinal neurodegenerative disorders which will require spinal cell, vector or drug delivery. Unlike conventional methods which require multiple injection sites to make multiple, localized substrate deliveries, the delivery devices and methods of the present invention may allow for multiple substrate delivery locations with homogeneous substrate delivery with a single injection site.

17 Claims, 4 Drawing Sheets

SPINAL MULTISEGMENTAL CELL AND DRUG DELIVERY SYSTEM

CROSS-REFERENCE TO RELATED APPLICATION

This application claims benefit of U.S. Provisional Application having application No. 60/915,743 filed May 3, 2007, which is hereby incorporated by reference herein in its entirety.

STATEMENT OF GOVERNMENT INTEREST

This invention was made with government support under NS051644 awarded by the National Institutes of Health. The government has certain rights in the invention.

BACKGROUND OF THE INVENTION

The present invention generally relates to a drug or cell delivery system and more specifically, to a drug or cell delivery system for multisegmental injection of substrate and/or cells into an animal or human.

Currently used devices employ multiple vertical spinal cord injections to deliver cells into multiple spinal cord segments. (Feron et al., Brain, 2005: 128: 2951-2960.) The risk of secondary spinal cord injury resulting from multiple vertical injections is high as it can lead to a mechanical trauma of otherwise intact and functional spinal cord tissue.

Previous devices developed for multiple depositions of cells into brain tissue have used plastic injection cannulas which bends after exiting the guide needle and therefore do not permit deposition of the injectate in a single plane (if measured against the guide needle). See FIG. 2C of Brecknell and Fawcett, Experimental Neurology, 1996; 138: 338-343.

The second type of device which was developed for brain injections describes the use of a rigid type of guide needle which can hold a specific angle (shape) and can be used for guided placement of flexible injection needle or possibly for injections. See page 1498—Material and Methods section of Cunningham et al., Neurosurgery, 2004; 54: 1497-1507.

As can be seen, there is a need for apparatus and methods for delivering a substrate into the spinal cord of a mammal while minimizing the number of required injection sites.

SUMMARY OF THE INVENTION

In one aspect of the present invention, a device for the delivery of a substrate into a spinal cord comprises a guide needle having an inside diameter; an injection needle fitting into the inside diameter of the guide needle; a stepping motor advancing the injection needle into and within the spinal cord; and a chamber containing the substrate or cells in fluid communication with the injection needle.

In another aspect of the present invention, a method for multisegmental delivery of a substrate or cells into a spinal cord comprises advancing a guide needle into the spinal cord; advancing an injection needle through the guide needle into the spinal cord; and withdrawing the injection needle while delivering the substrate or cells into the spinal cord.

In a further aspect of the present invention, a method for homogenous delivery of a substance into a spinal cord comprises advancing a guide needle into spinal parenchyma at an angle of about 45 degrees; advancing an injection needle through the guide needle horizontally into spinal parenchyma; initiating delivery of the substance or cells after the injection needle is fully inserted into spinal parenchyma (up to 1-3 inches); and continuing delivery of the substance or cells while the needle is withdrawn from spinal parenchyma using a computer-controlled stepping motor.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

As used herein, the term "substrate" refers to any injectable substance, including but not limited to cells, drugs, viruses, plasmids, growth factors and the like. The substrate may any suitable form of matter, including a liquid, a suspension, a gel, an encapsulated solid, a nanoparticle suspension, a slow- or extended-release polymer composition and the like.

As used herein, the term "mammal" refers to any class of warm-blooded higher vertebrates that includes humans.

As used herein, the term "horizontal" refers to a direction of the spinal column when a subject is lying supine or prone. In other words, horizontal may be described as along the long axis of the spine. The term "vertical" refers to a direction from about 45 degrees to about 90 degrees relative to the horizontal direction.

Broadly, the present invention may permit a multisegmental injection of cells or any diffusible substances (such as drugs, growth factors or any other injectable substance) into spinal cord in large animal species and in humans. The present invention may provide methods and apparatus so that one vertical spinal cord puncture may be required to permit a multisegmental (up to 4-6 spinal segments) delivery of a substrate.

Conventional devices employ multiple vertical spinal cord injections to deliver cells, drugs, vectors or the like into spinal cord parenchyma. In a typical setting, multiple injections (up to several hundred) are required to achieve a satisfactory cell, drug or vector delivery to multiple spinal segments (Feron et al., Brain, 2005: 128: 2951-2960.). The device of the present invention, after exiting the guide needle, the injection needle may retain a fixed angle, thus permitting a well controlled placement in a given plane over 1-3 inches from the tip of the guide needle.

The device of the present invention may permit the number of vertical injections to be reduced to about less than 20, typically less than 10, and even more typically to within a range of about 6 to 10. In addition, because of a continuous cell delivery during the process of the needle withdrawal, a much more homogeneous distribution of substrate can be achieved in the multiple spinal cord segments. The device of the present invention may use a stepping motor to withdraw the needle, thus permitting a homogenous injectate delivery over the whole injection trajectory.

Figure 1A:
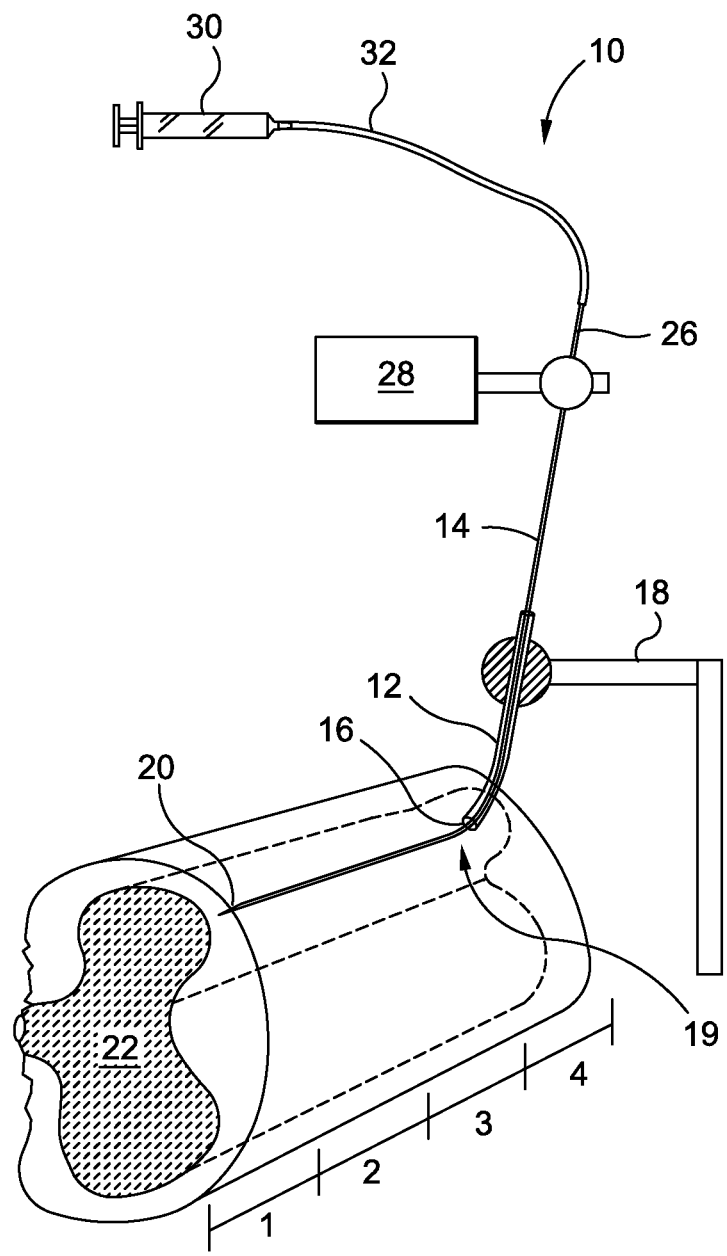
FIG. 1A is a graphical representation of a drug delivery system according to the present invention nearly fully injected into spinal segments.

Referring to FIG. 1A, a device 10 of the present invention may include two separate elements, a guide needle 12 and an injection needle 14. The guide needle 12 may be from about 27 to about 30 gauge, typically from about 100 to about 400 micrometers in diameter, and may be made from stainless steel or other non-corrosive material. The guide needle 12 may be from about 2 to about 4 inches long. The lower 2-3 inches of the needle may have a bend 16, the bend 16 curving circularly at an angle of about 45 degrees. The upper 3-4 inches of the needle may be attached firmly to a micromanipulator 18 which may be used to place the guide needle into a specific spinal cord region localized in the gray 22 or white matter.

The injection needle 14 may be made of stainless steel, polycarbonate, synthetic quartz polymer or other flexible material tubing between about 34 to about 30 gauge and may be from about 5 to about 7 inches long. One end of the needle (internal end 20) may be advanced into the spinal cord tissue (e.g., the gray matter 22) through the guide needle 12 and used for injection of a substrate 24, such as cells or any diffusible substances (see FIG. 1B). The other end (i.e., external end 26, about 1-2 inches) may be attached to a stepping motor 28. The stepping motor 28 may be used for advancement of the injection needle 14 into spinal parenchyma (e.g., gray matter 22) through the guide needle 12. The external end 26 of the injection needle 12 may be connected to a syringe 30 using polyethylene tubing 32. Injections may be performed by using a digital microinjector (not shown).

Figure 1B:
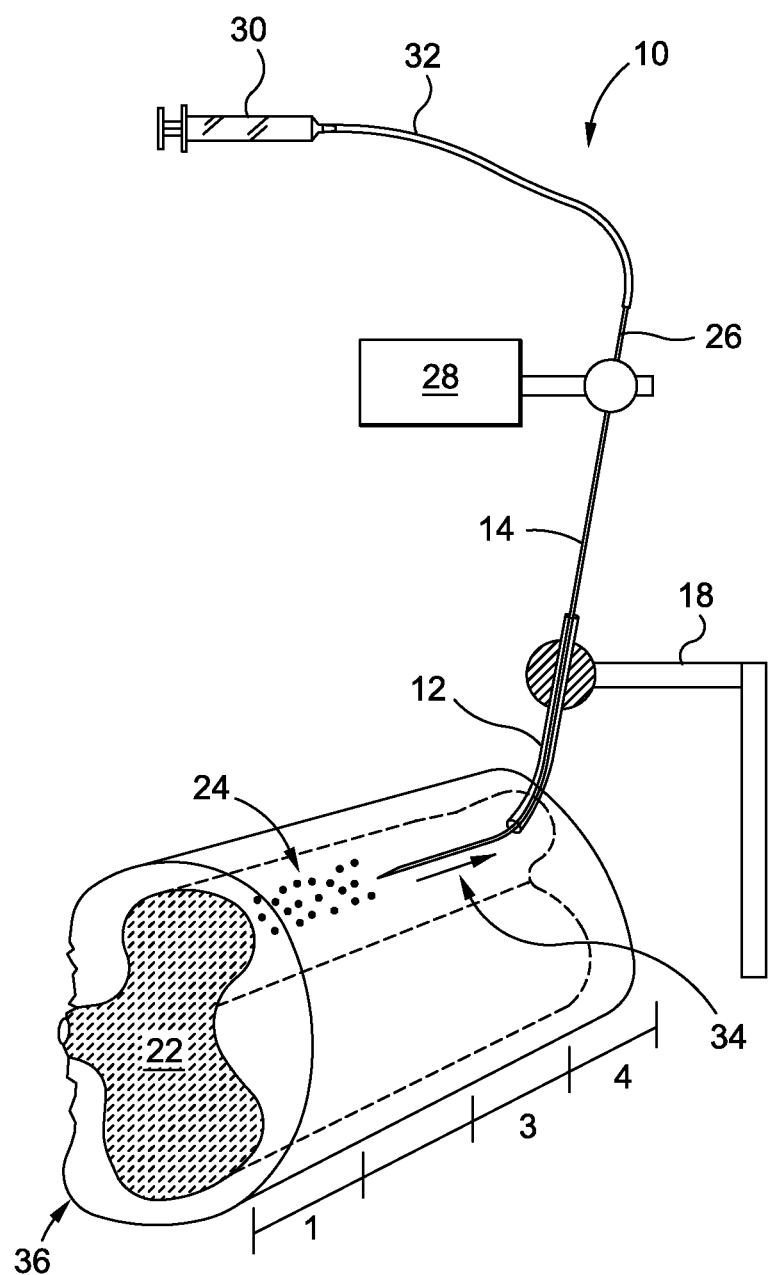
FIG. 1B is a graphical representation of the drug delivery system of FIG. 1A partially withdrawn from the spinal segments.
Figure 1C:
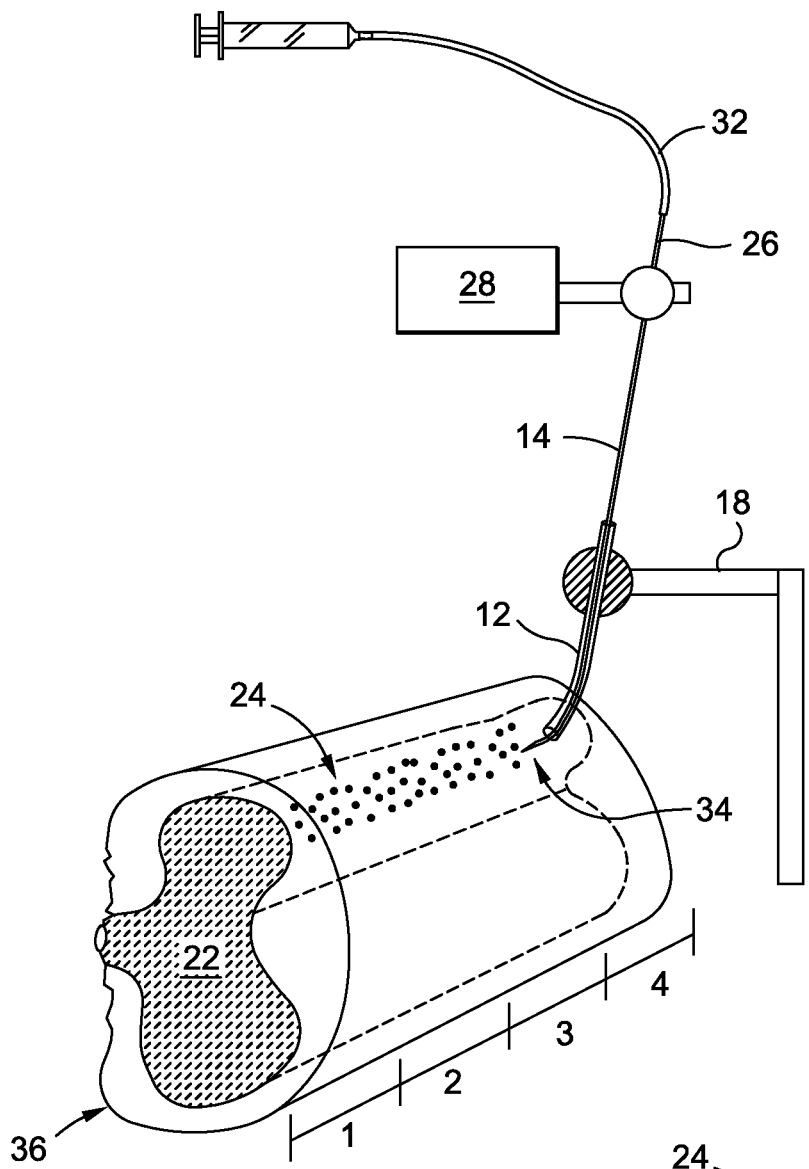
FIG. 1C is a graphical representation of the drug delivery system of FIG. 1A nearly fully withdrawn from the spinal segments.
Figure 1D:
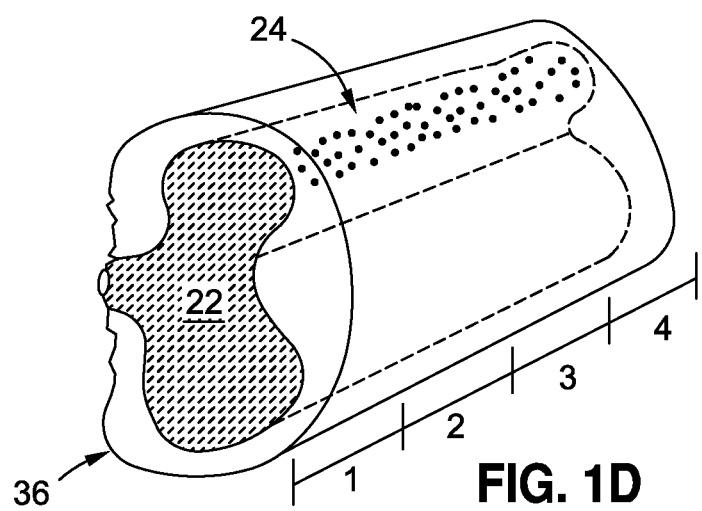
FIG. 1D is a graphical representation of the drug delivery system of FIG. 1A after the injection is completed.

Referring now to FIGS. 1B, 1C and 1D, the guide needle 12 may be advanced into spinal parenchyma (e.g., gray matter 22) through the dorsal horn (e.g., spinal segment number 4) of the spinal cord 32 at an injection angle (not shown) of about a 45 degree angle relative to horizontal. The tip (not shown) of the guide needle 12 may be targeted into the spinal regions to be injected with substrate 24. The tip of the guide needle 12 may have a bend 19 at an angle of about 45 degrees, which, along with the injection angle, may result in the tip of the guide needle 12 pointing in a substantially horizontal direction along the spinal cord 36 when inserted into a subject. The bend 19 in the tip may be formed along the guide needle 12 within the last 0.5 inches thereof, typically within the last 0.1-0.2 inch thereof. The spinal region may be gray matter 22 (dorsal horn, intermediate zone or ventral horn) or any region of the white matter.

After positioning of the guide needle 12, the injection needle 14 may be advanced horizontally into spinal parenchyma (e.g., gray matter 22) in dorso-caudal or caudo-rostral direction. The distance of the injection needle 14 advancement can be up to about 1 to about 3 inches.

After the targeted spinal segment is reached with the tip (internal end 20) of the injection needle 14, the injection of substrate 24 may be initiated using, for example, a microinjector (not shown). During the course of the injection, the injection needle may be gradually withdrawn, as shown by arrow 34, thereby permitting a homogenous multisegmental delivery of substrate 24 into the targeted areas (spinal segments 1-4), as shown in FIG. 1D.

Figure 2:
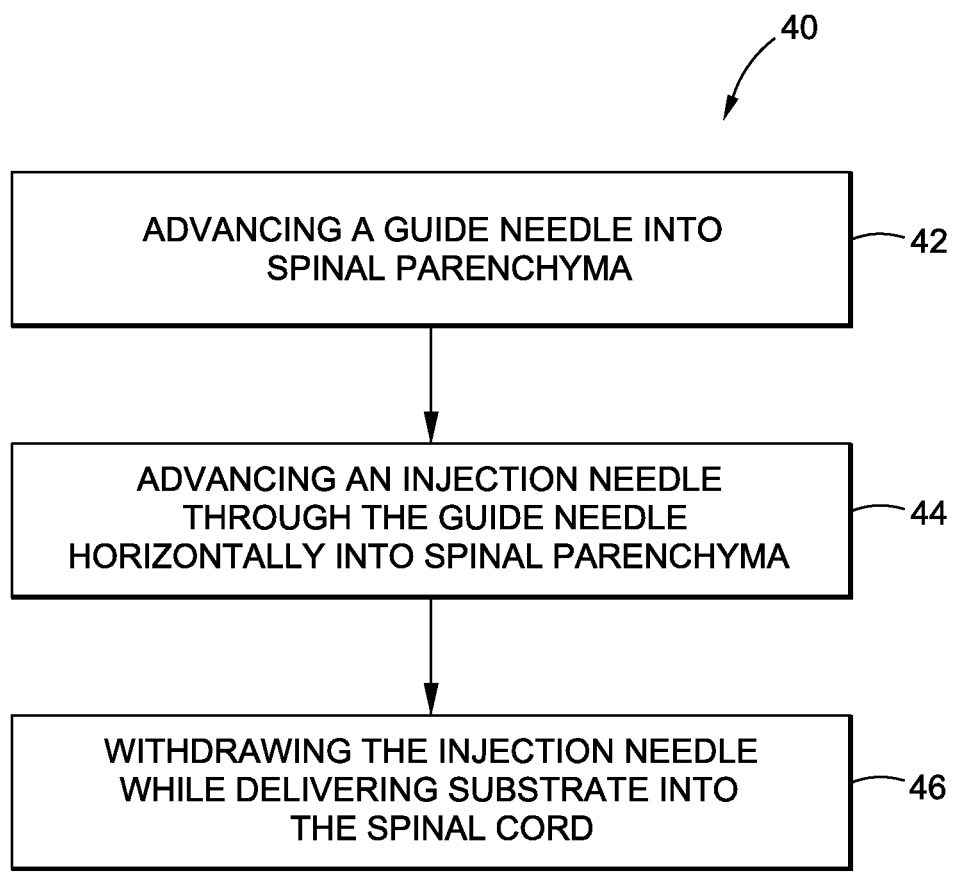
FIG. 2 is a flow chart describing a method according to the present invention.

Referring to FIG. 2, there is shown a flow chart of a method 40 for multisegmental delivery of a substance (e.g., substrate 24) into a spinal cord (e.g., spinal cord 36). The method may include a step 42 of advancing a guide needle (e.g., guide needle 12) into spinal parenchyma (e.g., gray matter 22). The guide needle may be bent at the injection end at an angle of about 45 degrees. The method may include a further step 44 of advancing an injection needle (e.g., injection needle 14) through the guide needle to exit the guide needle horizontally into spinal parenchyma. The injection needle may be injected through one or several spinal segments. The method may also include a step 46 of withdrawing the injection needle while delivering the substance into the spinal cord. This withdrawal during delivery may provide not only multisegmental delivery of the substance, but may also provide for a homogenous delivery of the substance. Conventional methods may fail to provide the multisegmental delivery or the homogenous delivery of the substance into the spinal column.

It should be understood, of course, that the foregoing relates to exemplary embodiments of the invention and that modifications may be made without departing from the spirit and scope of the invention as set forth in the following claims.

I claim:

1. A device for the delivery of a substrate into a spinal cord, the device comprising: a guide needle having an inside diameter; an injection needle fitting into the inside diameter of the guide needle; a stepping motor advancing and withdrawing the injection needle into and within the spinal cord, and a syringe capable of holding the substrate; wherein the stepping motor is attached to the injection needle between the syringe and a portion of the injection needle, wherein the guide needle has a bend at a tip of an injection end thereof.

2. The device of claim 1, further comprising a chamber containing the substrate in fluid communication with the injection needle.

3. The device of claim 1, wherein the bend is about 45 degrees.

4. The device of claim 1, wherein the guide needle is from about 27 to about 30 gauge.

5. The device of claim 1, wherein the injection needle is from about 100 to about 400 micrometers in diameter.

6. The device of claim 1, wherein the injection needle is from about 1 to about 3 inches long.

7. The device of claim 1, further comprising a micromanipulator for placing the guide needle into a specific spinal cord region.

8. A method for multisegmental delivery of a substrate into a spinal cord, the method comprising: advancing a guide needle into the spinal cord, the guide needle having a bend at an angle of about 45 degrees at an end thereof, the end being advanced into the spinal cord; advancing an injection needle through the guide needle and into the spinal cord with a stepping motor attached to the injection needle; injecting the substrate into the spinal cord through a syringe to the injection needle, wherein an external end of the injection needle is directly connected to the syringe with polyethylene tubing; and withdrawing the injection needle while delivering the substrate into the spinal cord; wherein the stepping motor is attached to the injection needle between the syringe and a portion of the injection needle inside the guide needle.

9. The method of claim 8, further comprising advancing the injection needle from about 1 to about 3 inches horizontally through the spinal cord.

10. The method of claim 8, wherein the substrate is selected from the group consisting of cells, drugs, viruses, plasmids and growth factors.

11. The method of claim 8, wherein the guide needle and the injection needle are advanced into spinal parenchyma.

12. The method of claim 8, further comprising delivering the substrate to the entire length of the spinal cord by repeating each of the steps at multiple injection sites, the number of injection sites being from about 6 to about 20.

13. A method for homogenous delivery of a substrate into a spinal cord, the method comprising: advancing a guide needle into spinal parenchyma at an injection angle of about 45 degrees, the guide needle having a bend of about 45 degrees within the last 0.5 inches of an insertion end thereof; advancing an injection needle through the guide needle horizontally into spinal parenchyma with a stepping motor attached to the injection needle; initiating delivery of the substrate to the injection needle with a syringe after the injection needle is fully inserted into spinal parenchyma; and continuing delivery of the substrate while the needle is withdrawn from spinal parenchyma, wherein the stepping motor is attached to the injection needle between the syringe and a portion of the injection needle inside the guide needle.

14. The method of claim 13, further comprising advancing the injection needle from about 1 to about 3 inches horizontally through the spinal cord.

15. The method of claim 13, further comprising delivering the substrate to the entire length of the spinal cord by repeating each of the steps at multiple injection sites, the number of injection sites being from about 6 to about 20.

16. The method of claim 15, further comprising positioning the guide needle with a micromanipulator for each of the steps of advancing a guide needle into spinal parenchyma.

17. The method of claim 13, wherein the substrate is delivered to multiple spinal segments in a single injection.

* * * * *